United States Patent [19]
Seino et al.

[11] Patent Number: 6,068,841
[45] Date of Patent: May 30, 2000

[54] ANTIBODIES TO FAS-L FOR TREATMENT OF HEPATITIS

[75] Inventors: Ken-ichiro Seino; Nobuhiko Kayagaki; Hideo Yagita; Ko Okumura, all of Tokyo; Motomi Nakata, Kanagawa, all of Japan

[73] Assignee: Sumitomo Electric Industries, Ltd., Osaka, Japan

[21] Appl. No.: 09/065,059

[22] PCT Filed: Oct. 24, 1996

[86] PCT No.: PCT/JP96/03089

§ 371 Date: Apr. 27, 1998

§ 102(e) Date: Apr. 27, 1998

[87] PCT Pub. No.: WO97/15326

PCT Pub. Date: May 1, 1997

[30] Foreign Application Priority Data

Oct. 27, 1995 [JP] Japan ................................. 7-303491

[51] Int. Cl.$^7$ ..................... A61K 39/395; C07K 16/18
[52] U.S. Cl. ................... 424/145.1; 424/133.1; 424/152.1; 530/387.3; 530/388.23
[58] Field of Search ................. 424/133.1, 152.1, 424/145.1; 530/387.3, 388.23

[56] References Cited

U.S. PATENT DOCUMENTS 5,830,469 11/1998 Lunch et al. ..................... 424/144.1

FOREIGN PATENT DOCUMENTS

| | | |
|---|---|---|
| 0 120 694 A2 | 10/1984 | European Pat. Off. . |
| 0 125 023 A1 | 11/1984 | European Pat. Off. . |
| 0 171 496 A2 | 2/1986 | European Pat. Off. . |
| 0 173 494 A2 | 3/1986 | European Pat. Off. . |
| 0497001 A2 | 8/1992 | European Pat. Off. . |
| 0 675 200 A1 | 10/1995 | European Pat. Off. . |
| 675200 | 10/1995 | European Pat. Off. . |
| 0872488 A1 | 10/1998 | European Pat. Off. . |
| 6-327491 | 11/1994 | Japan . |
| WO 86/01533 | 3/1986 | WIPO . |
| WO 95/18819 | 7/1995 | WIPO . |
| WO 95/27735 | 10/1995 | WIPO . |
| WO 96/29350 | 9/1996 | WIPO . |

OTHER PUBLICATIONS

Takahashi, T. et al. Human Fas ligand: Gene structure, chromosomal location and species specificity. International Immunology vol. 6, pp. 1567–1574, Oct. 25, 1994.

"Purification and Characterization of the Fas–ligand that Induces Apoptosis", Suda et al., J. Exp. Med., vol. 179, No. 3, pp. 873–879, Mar. 1994.

"The Fas Death Factor", Nagata et al., Science, vol. 267, No. 5203, pp. 1449–1456, Mar. 10, 1995.

"Hepatitis and Apoptosis", Eiji Mita et al., Experimental Medicine, vol. 13, No. 16, Oct. 20, 1995, pp. 200–204, abstract only.

"The Polypeptide Encoded by the cDNA for Human Cell Surface Antigen Fas Can Mediate Apoptosis", Itoh et al., Cell, vol. 66, Jul. 26, 1991, pp. 233–243.

"Anti–Fas monoclonal antibody is cytocidal to human immunodeficiency virus–infected cells without augmenting viral replication", Kobayashi et al., Proc. Natl. Acad. Sci., vol. 87, Dec. 1990, pp. 9620–9624.

"Lethal effect of the anti–Fas antibody in mice", Nature, vol. 364, Aug. 26, 1993, pp. 806–809.

S. Yonehara et al., "A Cell–Killing Monoclonal Antibody (Anti–Fas) to a Cell Surface Antigen Co–Downregulated with the Receptor of Tumor Necrosis Factor", *J. Exp. Med.*, vol. 169, May 1989, pp. 1747–1756.

"Apoptosis–Mechanism of Cell Death", Experimental Medicine, vol. 11, No. 17, 1993, pp. 61–66, Abstract only.

Gayle C. Bosma et al., "A severe combined immunodeficiency mutation in the mouse", *Nature*, vol. 301, Feb. 10, 1983, pp. 527–530.

Sheri M Krams et al., "Generation of Biliary Lesions after Transfer of Human Lymphocytes into Severe Combined Immunodeficient (SCID) Mice", *J. Exp. Med.*, vol. 170, Dec. 1989, pp. 1919–1930.

Michael A. Duchosal et al., "Transfer of Human Systemic Lupus Erythematosus in Severe Combined Immunodeficient (SCID) Mice", *J. Exp. Med.*, Sep. 1990, pp. 985–988.

L. Macht et al., "Severe combined immunodeficient (SCID) mice: a model for investigating human thyroid autoantibody synthesis", *Clin. exp. Immunol.*, vol. 84, 1991, pp. 34–42.

L. Presta et al., "Helix Signals in Protein", *Science*, vol. 240, Jun. 1988, pp. 1632–1639.

A.E. Ringwood, "Terrestrial origin of the Moon", *Nature*, vol. 322, Jul. 1986, pp. 323–327.

Peter T. Jones et al., "Replacing the complementarily–determining regions in a human antibody with those from a mouse", *Nature*, vol. 321, May 1986, pp. 522–525.

S. Roberts et al., "Generation of an antibody with enchanced affinity and specificity for its antigen by protein engineering", *Nature*, pp. 741–734, 1987.

*Primary Examiner*—David Saunders
*Attorney, Agent, or Firm*—McDermott, Will & Emery

[57] ABSTRACT

The invention provides therapeutic agents for hepatitis, comprising an antibody against a human Fas ligand, or an active fragment thereof as an active ingredient. The therapeutic agents for hepatitis according to the invention are particularly effective for the treatment of hepatitis caused by the death of hepatocytes due to apoptosis among many kinds of hepatitis.

3 Claims, 3 Drawing Sheets

Fig. 4

```
                                                      CDR1               CDR2
NOK1VH .amino   1:VQLQESGPELVKPGASVKISCKASGYAF--SSSWMNWVKQRPGKGLEWIGRIYPGDGDTN    58
NOK2VH .amino   1:VQLQQSGAELVRPGTSVKMSCKAAGYTF--TNYWIGWVKQRPGHGLEWIGYLYPGGLYTN    58
NOK3VH .amino   1:VKLQESGPELVKPGASVKISCKASGYAF--SSSWMNWVKQRPGKGLEWIGRIYPVNGDTN    58
NOK4VH .amino   1:VQLQESGPGLVKPSQSLSLTCSVTGYSITSGYYW-NWIRQFPGNKLEWMG-YISYDGSNN    58
NOK5VH .amino   1:VQLQESGAEPAKPGASVKMSCKASGYTF--TTYWMHWVKQRPGQGLEWIGYINPSSGYTE    58
                  * ** **       *   * * **      *  *   * ** ***  *
                                                           CDR3
NOK1VH .amino  59:DNGKFKGKATLTADKSSSTAYMQLSSLTSEDSAVYFCARSYYYDSPW-FTYWGQGTTVT  117
NOK2VH .amino  59:YNEKFKGKATLTADTSSSTAYMQLSSLTSEDSAIYYCARYRDYD-YAMDY--WGQGTTVT  115
NOK3VH .amino  59:YNGKFKGKATLTADKSSSTAYMQLSSLTSEDSAVYFCA-T---DGY-WYFDVWGQGTTVT  113
NOK4VH .amino  59:YNPSLKNRISITRDTSKNQFFLKLNSVTTEDTATYYCA-VYYYDG--SSFDYWGQGTTVT  115
NOK5VH .amino  59:YNQKFKDKATLTADKSSSTAYMQLISLTSEDSAVYYCARRGNY--YYFDY--WGQGTTVT  114
                  *  *     * * *     * * ** *  * **          *******

NOK1VH .amino 118:VSS   120
NOK2VH .amino 116:VSS   118
NOK3VH .amino 114:VSS   116
NOK4VH .amino 116:VSS   118
NOK5VH .amino 115:VSS   117
                  ***
```

Fig. 5

```
                                                      CDR1               CDR2
NOK1VL .amino   1:DIQMTQSPSSLSASLGDRVTISCRASQDISNY-----LNWYQQKPDGTVKLLIYYTSRLH    55
NOK2VL .amino   1:DVLMTQTPLSLPVNIGDQASISCKSTKSLLNSDGFTYLGWCLQKPGQSPQLLIYLVSNRF    60
NOK4VL .amino   1:DIVLTQSPASLAVSLRQRATISCRASEGVDSY-GISFMHWYQQKPGQPPKLLIYRASYLK    59
NOK5VL .amino   1:DVLMTQTPKFLPVSAGDRVTMTCKASQS-V---G-NNVAWYQQKPGQSPKLLIYYTSNRY    55
                  *  ** *  *                  *            *  ***   ****  *
                                                           CDR3
NOK1VL .amino  56:SGVPSRFSGSGSGTDYSLTISNLEPEDIATYFC-QQYSEFPWTFGGGTKLEIKR   108
NOK2VL .amino  61:SGVPDRFSGSGSGTDFTLKISRVEAEDLGVYYCFQSNY-LPLTFGSGTKLEIKR   113
NOK4VL .amino  60:SGVPARFSGSGSRTDFTLTIDPVEADDAATYYC-QQNNEDPWTFGGGTKLEIKR   112
NOK5VL .amino  56:TGVPDRFTGSGSGTDFTFTISSVQVEDLAVYFC-QQHYSSPYTFGSGTKLE---   105
                  ***  ** **** **    *     *   * *   *  *  *** *****
```

# ANTIBODIES TO FAS-L FOR TREATMENT OF HEPATITIS

This application is a 371 of PCT/JP96/03089, filed Oct. 24, 1996, which claims priority to Japanese Application No. 303491, filed Oct. 22, 1995.

TECHNICAL FIELD

The present invention relates to therapeutic agents for hepatitis, and in particular to therapeutic agents for hepatitis, comprising an antibody against a human Fas ligand (hereinafter may be abbreviated as "FasL"), or an active fragment thereof as an active ingredient. The therapeutic agents for hepatitis according to the present invention are particularly effective for the treatment of hepatitis caused by the death of hepatocytes due to apoptosis among many kinds of hepatitis.

PRIOR ART

Multicellular organisms skillfully control the proliferation and death of cells to maintain their homeostasis. Many cells are removed by cell death in the course of ontogeny. In an adult, organ constituting cells always maintain their functions while well keeping a balance between their proliferation and death. Such cell death is preliminarily programmed death called "programmed cell death". On the other hand, cell death caused by physical or chemical factors is called "accidental cell death" and is distinguished from the programmed cell death.

These two deaths are different from each other in process. In the programmed cell death, cells are considered to die via the process of apoptosis defined by morphological features such as reduction in cell volume, disappearance and pycnosis of nuclear reticular structure, disappearance of microvilli and formation of vesicles on a cell surface, and formation of apoptotic bodies subsequent thereto. In many cases, the apoptosis is accompanied by a fragmentation reaction of a chromosomal DNA. On the other hand, in the accidental cell death, cells are considered to die via a process of necrosis in which cells and nuclei are imbibed and destroyed.

However, cell death by anticancer agents and radiation, cell death by viral infection or the death of target cells by cytotoxic lymphocytes has been known to go through the process of apoptosis though it is by no means considered to be programmed cell death. At present, this fact had led to the thought that the apoptosis is not always identical with the programmed cell death, and so both have come to be distinguished from each other.

At present, many have been known as factors or substances which induce apoptosis. Fas (Fas antigen) is known as a cell-surface protein that mediates apoptosis. The Fas is isolated as a cell-surface protein that mediates a signal of death to cells, and is a type I transmembrane protein belonging to the TNF/NGF receptor family and having a molecular weight of 45 kDa. Most of members of the TNF/NGF receptor family are considered receptors for their specific ligands. The Fas is also considered a receptor or a ligand mediating a signal of apoptosis. Cells in which Fas has been expressed are led to death by switching on apoptosis due to binding of the Fas to its ligand, Fas ligand.

The Fas ligand is a physiological ligand of Fas and is a cell-surface protein of 40 kDa. The Fas ligand is known from its structure to belong to the TNF family. The Fas ligand has activity to induce apoptosis to cells in which Fas has been expressed.

A system of Fas and Fas ligand (namely, Fas system) is a field in which investigations as to the apoptosis have been most evolved to date, and many investigation reports have been made. For example, the fact that Fas plays the role of a switch in apoptosis may go back to a paper by Yonehara, et al. on the production of anti-Fas antibody (J. Exp. Med., Vol. 169, pp. 1747–1756, 1989). After that, the structure of Fas has been clarified by cloning of the Fas gene (Cell, Vol. 66, pp. 233–243, 1991). Further, it has been reported that the expression of Fas is recognized in T cells infected with HIV which is a causative virus of AIDS (Proc. Natl. Acad. Sci., U.S.A., Vol. 87, pp. 9620–9624, 1990), and that when an anti-Fas antibody (Jo-2 antibody) is administered to mice, the mice undergo a phenomenon similar to fulminant hepatitis to die (Nature, Vol. 364, pp. 806–809, 1993). Besides these, various investigation reports have been made. These reports are collected in detail in "Apoptosis-Mechanism of Cell Death" in Experimental Medicine, Vol. 11, No. 17, 1993, Yodo-sha; and "The Forefront of Apoptosis Study—from Signal Transfer Mechanism to Disease" in Experimental Medicine, Vol. 13, No. 16, 1995, Yodo-sha.

With respect to hepatitis, various reports have been made in addition to the attack of fulminant hepatitis by administration of the anti-Fas antibody (Jo-2 antibody) to mice as described above. The contents of these reports are collected as a paper entitled "Hepatitis and Apoptosis" in Experimental Medicine, Vol. 13, No. 16, pp. 200–204, 1995. According to this paper, the following facts have been elucidated as to hepatitis.

(1) In chronic hepatitis, piecemeal necrosis serving as an index to activity is recognized about a portal region. However, the whole of cell death caused in this region is apoptosis, and not necrosis.

(2) With respect to the cytotoxic mechanism in viral hepatitis, cellular immunity plays an important role. A viral antigen is processed in an infected hepatocyte and then presented on the surface of the hepatocyte by an HLA class I, and CTL recognizes and kills this.

(3) It is considered that there is a possibility that apoptosis via a Fas system may participate in hepatocyte cytotoxicity by a hepatitis virus, namely, a possibility that lymphocytes infiltrated into the liver may express a Fas ligand to induce apoptosis to hepatocytes in which a Fas antigen has been expressed.

(4) An investigation as to the expression of Fas antigen in hepatitis B and C tissues by means of an immunohistological technique making use of an anti-Fas antibody (mouse monoclonal antibody, IgM fraction) has revealed that the expression of Fas antigen in the hepatitis B and C tissues correlates to the activity of hepatitis.

(5) In chronic hepatitis C, monocytes infiltrated into the liver mean that a Fas ligand, which can induce apoptosis, is presented in hepatocytes in which a Fas antigen has been expressed and suggest that apoptosis via a Fas system participates in the hepatocytotoxic mechanism.

As described above, it has been known that in viral hepatitis, the Fas antigen is expressed to a great extent irrespective of type B and type C. However, with respect to the mechanism of induction by the Fas ligand, many points such as intracellular signal are unknown and remain problems to be studied after this under the circumstances.

DISCLOSURE OF THE INVENTION

It is an object of the present invention to provide a therapeutic agent for hepatitis, which is particularly effective for the treatment of hepatitis caused by the death of hepatocytes due to apoptosis among many kinds of hepatitis.

The present inventors have thought that the system (Fas system) of Fas and Fas ligand participates in an attack of fulminant hepatitis or viral hepatitis in the liver as described above, and carried out an extensive investigation using antibodies against the Fas ligand. As a result, it has been found that the Fas ligand damages hepatocytes in an in vitro experimental system, and this damage can be inhibited by an anti-Fas ligand antibody. Besides, it has been newly found that the antibody against Fas ligand can prevent an attack of hepatitis. It has further been found that a preparation comprising this antibody as an active ingredient is useful as a therapeutic agent (antihepatitis agent) for hepatopathy such as viral hepatitis. The present invention has been led to completion on the basis of these findings.

According to the present invention, there is provided a therapeutic agent for hepatitis, comprising an antibody against a human Fas ligand, or an active fragment thereof as an active ingredient.

According to the present invention, there are also provided the following preferred embodiments.

1. The therapeutic agent for hepatitis, wherein the antibody against human Fas ligand, or the active fragment thereof is a monoclonal antibody which specifically reacts to the Fas ligand, or an active fragment thereof.

2. The therapeutic agent for hepatitis, which inhibits apoptosis of the liver caused by binding of the Fas ligand to hepatocytes in which Fas has been expressed.

3. The therapeutic agent for hepatitis, which improves the levels of GOT and GPT in blood, thereby improving the function of the liver.

4. The therapeutic agent for hepatitis, wherein the active fragment of the antibody against human Fas ligand is at least one selected from the group consisting of F(ab')$_2$, Fab', Fab, Fv and recombinant Fv.

5. The therapeutic agent for hepatitis, wherein the monoclonal antibody, which specifically reacts to the human Fas ligand, is a monoclonal antibody produced by any one of respective hybridoma cell lines deposited as Accession Nos. FERM BP-5044, FERM BP-5045, FERM BP-5046, FERM BP-5047 and FERM BP-5048 in National Institute of Bioscience and Human-Technology, Agency of Industrial Science and Technology.

6. The therapeutic agent for hepatitis, which is a chimera antibody molecule at least containing a hypervariable region of the monoclonal antibody.

7. The therapeutic agent for hepatitis, which is a chimera antibody molecule at least containing a variable region of the monoclonal antibody.

BRIEF DESCRIPTION OF THE DRAWINGS

FIG. 4 illustrates amino acid sequences of VH regions (H chains) of monoclonal antibodies, NOK1 to NOK5 SEQ ID NOS:1, 5, 9, 11 and 15, wherein portions enclosed with a rectangle represent hypervariable regions (CDR1 to CDR3).

FIG. 5 illustrates amino acid sequences of VL regions (L chains) of monoclonal antibodies, NOK1 SEQ ID NO:3, NOK2 SEQ ID NO:7, NOK4 SEQ ID NO:13 4 and NOK5 SEQ ID NO:7, wherein portions enclosed with a rectangle represent hypervariable regions (CDR1 to CDR3).

BEST MODE FOR CARRYING OUT THE INVENTION

Figure 1:
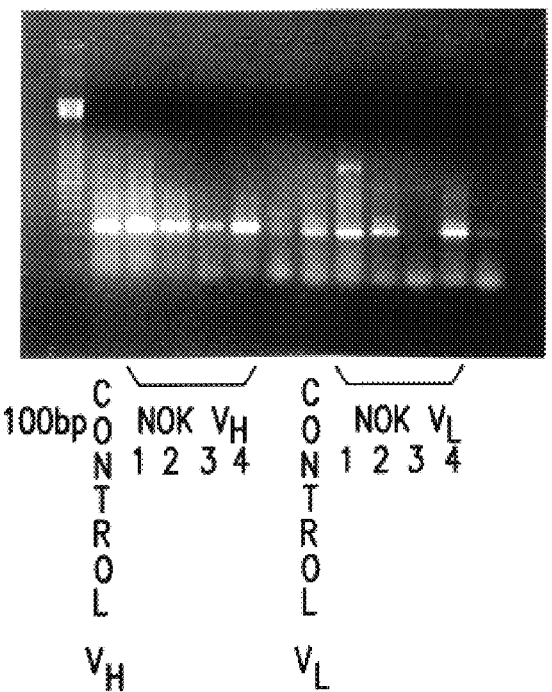
FIG. 1 is a mini gel electrophorogram of reaction mixtures in PCR of VH genes and VL genes of anti-FasL antibodies.

The antibody against a Fas ligand (i.e., anti-FasL antibody), which is used as an active ingredient for the therapeutic agent for hepatitis according to the present invention, is an antibody which recognizes the Fas ligand which is a cell-surface molecule, and a soluble Fas ligand (sFasL) present in a cell-culture supernatant liquid or a body fluid of the living body by decomposition by a matrix metalloprotease. A monoclonal antibody which specifically reacts to the Fas ligand is preferred as the antibody against Fas ligand. An antibody which can inhibit the binding of the Fas ligand to Fas is more preferred. Such a monoclonal antibody can be provided, for example, in accordance with the following process.

(1) An animal (for example, a rodent such as a mouse) is immunosensitized with COS cells in which a Fas ligand has been expressed. However, the animal should be defective in the function of Fas.

(2) Antibody-producing cells are prepared from the immunosensitized animal to form a suspension thereof. Splenocytes or lymphadenocytes are mainly used. However, peripheral lymphocytes may also be used. When splenocytes are used, the spleen is taken out of the immunosensitized rodent to form a suspension of splenocytes.

(3) The suspension of the antibody-producing cells is mixed with myeloma cells to fuse both cells. For example, the suspension of the splenocytes is mixed with myeloma cells of a mouse in the presence of a hybridization accelerator (for example, polyethylene glycol) to fuse both cells. The cell fusion may be conducted by an electrical treatment. As the myeloma cells used herein, those (for example, 8-azaguanine-resistant strain) distinguishable from the antibody-producing cells in a subsequent selective culture are used.

(4) The fused cells are diluted with a medium which does not favor unfused myeloma cells to culture the fused cells, thereby sorting hybridomas produced by the fusion of the antibody-producing cell with the myeloma cell. More specifically, the fused cells are cultured in a selective medium in which the antibody-producing cells are viable, but the myeloma cells are killed, thereby sorting hybridomas produced by the fusion of the antibody-producing cell with the myeloma cell. For example, when 8-azaguanine-resistant myeloma cells are used, an HAT medium (i.e., hypoxanthine-aminopterine-thymidine containing medium) is generally used as the selective medium.

(5) Whether antibodies secreted in a culture supernatant liquid containing the hybridomas are against the desired antigen or not is determined by using, as an indicator, the fact that the antibodies inhibit the attack of a Fas ligand present in a supernatant of Fas ligand-expressed COS cells against Fas-expressed cells.

(6) A series of cells in culture wells in which cells secreting the desired antibodies exist is cloned. The cloning is generally performed by the limiting dilution technique.

(7) A clone from which the desired antibody is secreted is selected.

(8) Cloning is conducted again to establish a hybridoma clone which secretes a monoclonal antibody against the desired antigen.

(9) The monoclonal antibody is prepared from a culture supernatant liquid of the hybridoma or an ascites fluid obtained by intraperitoneally administering the hybridoma to a mouse (for example, a nude mouse).

Examples of the monoclonal antibodies, which are used as an active ingredient for the therapeutic agents for hepatitis according to the present invention, include respective monoclonal antibodies (NOK1 to NOK5) produced by hybridoma cell lines respectively deposited as Accession Nos. FERM BP-5044 (Hybridoma NOK1), FERM BP-5045 (Hybridoma NOK2), FERM BP-5046 (Hybridoma NOK3), FERM BP-5047 Hybridoma NOK4) and FERM BP-5048 (Hybridoma NOK5) in National Institute of Bioscience and Human-Technology, Agency of Industrial Science and Technology.

The antibody against human Fas ligand is an immunoglobulin. The monoclonal antibody which specifically reacts to the human Fas ligand is a homogeneous immunoglobulin, and examples thereof include ① those belonging to the IgM class and having an L chain which is a κ chain, ② those belonging to the $IgG_{2a}$ subclass and having an L chain which is a κ chain, ③ those belonging to the $IgG_1$ subclass and having an L chain which is a κ chain, and ④ those belonging to the $IgG_3$ subclass and having an L chain which is a κ chain.

The active fragment of the antibody against Fas ligand means a fragment of an immunoglobulin having the antigen-antibody reaction activity of the anti-Fas ligand antibody. Specific examples of such an active fragment include $F(ab')_2$, Fab', Fab, Fv and recombinant Fv. These active fragments can be prepared from an immunoglobulin in accordance with a method known per se in the art. For example, the $F(ab')_2$ fragment can be obtained by digesting an immunoglobulin IgG with pepsin. The Fab' fragment can be obtained by reducing the $F(ab')_2$ fragment with a reagent such as 2-mercaptoethanol and alkylating the reduced product with monoiodoacetic acid. The Fab fragment can be obtained by digesting the IgG with papain. The Fv fragment can be obtained by bonding an H chain variable region (VH) and an L chain variable region ($V_L$) to each other by a nonconjugate bond. The recombinant Fv fragment can be obtained, for example, by sequencing DNAs as to genes corresponding to the H chain and L chain variable regions of the antibody from a hybridoma which produces a monoclonal antibody to determine base sequences which encode the H chain variable region ($V_H$) and the L chain variable region ($V_L$), respectively, and then integrating these DNA fragments in a vector to produce a monovalent active antibody fragment having a $V_H$-Linker-$V_L$ structure in *Escherichia coli* and cells such as animal cells.

The SCID mice used in Examples of the present invention are famous as an animal capable of transplanting human cells thereto. The SCID mouse is a mouse discovered as an immunodeficiency mutant mouse having no mature lymphocytes (T cells and B cells) by Bosma, et al. in 1983 (Nature, Vol. 301, pp. 527–530, 1983). This mouse shows the same morbid state as human severe combined immunodeficiency (SCID). There is a movement to transfer lymphocytes or lymphoid tissue of a patient suffering from primary biliary cirrhosis SLE, autoimmune thyroiditis or the like, which is a human autoimmune disease, into this SCID mouse to attempt to reproduce the nature of the disease. These are described in J. Exp. Med., Vol. 170, pp. 1919–1930, 1989; J. Exp. Med., Vol. 172, pp. 985–988, 1990; Clin. Exp. Immunol., Vol. 84, pp. 34–42, 1991; and the like. A similar attempt is reported in Science, Vol. 240, pp. 1632–1639, 1988.

The present inventors have succeeded in causing hepatitis by intraperitoneally administering human peripheral blood mononuclear cells (PBMC) to an SCID mouse and then intraperitoneally administering 20 mg/mouse of D-galactosamine and 10 μg/mouse of SEB (staphylococcal enterotoxin B) to the same mouse. This system is a system that the human PBMC is transferred into the SCID mouse in which Fas has been expressed, and the mouse is stimulated by D-galactosamine and SEB so as to activate T cells in the human PBMC transferred to express a Fas ligand on the surfaces of the cells, and moreover to secrete a soluble Fas ligand into the abdominal cavity and humor of the mouse, whereby Fas-expressed mouse hepatocytes are killed due to apoptosis via the Fas ligand, so that hepatitis is caused.

The therapeutic agent for hepatitis according to the present invention is considered an agent by which apoptosis of the liver caused by binding of the Fas ligand to hepatocytes, in which Fas has been expressed, is inhibited thereby curing hepatitis. More specifically, in the Fas-expressed hepatocytes, apoptosis is switched on by binding of the Fas to the Fas ligand. However, the therapeutic agent for hepatitis according to the present invention is considered to inhibit such a reaction, thereby curing hepatitis. The therapeutic agent for hepatitis according to the present invention can also improve the levels of GOT (glutamic-oxaloacetic transaminase) and GPT (glutamic-pyruvic transaminase) in blood. Specifically, the therapeutic agent for hepatitis according to the present invention can recover the GOT and GPT levels in blood to normal values.

When the monoclonal antibody (anti-FasL antibody) against human Fas ligand, or the active fragment thereof used in the present invention is caused to act as a therapeutic agent for hepatitis on the human, it is effective to humanize or chimerize the anti-FasL antibody or the active fragment thereof in order to prevent the production of any antibodies against extrinsic proteins such as HAMA (Human anti mouse antibody) to cause it to effectively act. The techniques concerning this have been already described in known literature or patent documents and can be practiced with ease so long as an antibody producing hybridoma is present. The patent documents include EP-A-0120694, EP-0125023, EP-0171496, EP-A-0173494 and WO86/01533, while the general literature includes Nature, Vol. 322, pp. 323–327 (1988), Nature, Vol. 321, pp. 522–525 (1986) and Nature, Vol. 328, pp. 731–734 (1987). The anti-FasL antibody or the active fragment thereof can be humanized or chimerized on the basis of the known techniques disclosed in these literature.

Upon the humanization or chimerization, it is preferable to include at least one of amino acid sequences of variable regions or hypervariable regions of respective monoclonal antibodies (NOK1 to NOK5) produced by hybridoma cell lines respectively deposited as Accession Nos. FERM BP-5044 (Hybridoma NOK1), FERM BP-5045 (Hybridoma NOK2), FERM BP-5046 (Hybridoma NOK3), FERM BP-5047 (Hybridoma NOK4) and FERM BP-5048 (Hybridoma NOK5) in National Institute of Bioscience and Human-Technology, Agency of Industrial Science and Technology.

The amino acid sequences of respective variable regions and hypervariable regions of the H chains and L chains of such monoclonal antibodies NOK1 to NOK5, and base sequences thereof have been discovered by the present inventors and are set forth in SEQUENCE LISTING.

(1) The H chain hypervariable regions of a monoclonal antibody produced by Hybridoma NOK1 extend ① from Ser of the 30th to Asn of the 34th, ② from Arg of the 49th to Gly of the 65th and ③ from Tyr of the 93rd to Tyr of the 109th of the amino acid sequence represented by SEQ ID NO:1 of SEQUENCE LISTING, and the L chain hypervariable regions thereof extend ① from Arg of the 24th to Asn of the 34th, ② from Tyr of the 50th to Ser of the 56th and ③ from Gln of the 89th to Thr of the 97th of the amino acid sequence represented by SEQ ID NO:3 of SEQUENCE LISTING.

(2) The H chain hypervariable regions of a monoclonal antibody produced by Hybridoma NOK2 extend ① from Asn of the 30th to Gly of the 34th, ② from Tyr of the 49th to Gly of the 65th and ③ from Tyr of the 93rd to Tyr of the 107th of the amino acid sequence represented by SEQ ID NO:5 of SEQUENCE LISTING, and the L chain hypervariable regions thereof extend ① from Lys of the 24th to Gly of the 39th, ② from Leu of the 55th to Ser of the 61st and ③ from Gln of the 95th to Thr of the 102nd of the amino acid sequence represented by SEQ ID NO:7 of SEQUENCE LISTING.

(3) The H chain hypervariable regions of a monoclonal antibody produced by Hybridoma NOK3 extend ① from Ser of the 30th to Asn of the 34th, ② from Arg of the 49th to Gly of the 65th and ③ from Tyr of the 93rd to Val of the 105th of the amino acid sequence represented by SEQ ID NO:9 of SEQUENCE LISTING.

(4) The H chain hypervariable regions of a monoclonal antibody produced by Hybridoma NOK4 extend ① from Tyr of the 32nd to Asn of the 35th, ② from Tyr of the 50th to Asn of the 65th and ③ from Tyr of the 93rd to Tyr of the 107th of the amino acid sequence represented by SEQ ID NO:11 of SEQUENCE LISTING, and the L chain hypervariable regions thereof extend ① from Arg of the 24th to His of the 38th, ② from Arg of the 54th to Ser of the 60th and ③ from Gln of the 93rd to Thr of the 101st of the amino acid sequence represented by SEQ ID NO:13 of SEQUENCE LISTING.

(5) The H chain hypervariable regions of a monoclonal antibody produced by Hybridoma NOK5 extend ① from Thr of the 30th to His of the 34th, ② from Tyr of the 49th to Asp of the 65th and ③ from Tyr of the 93rd to Tyr of the 106th of the amino acid sequence represented by SEQ ID NO:15 of SEQUENCE LISTING, and the L chain hypervariable regions thereof extend ① from Lys of the 24th to Ala of the 34th, ② from Tyr of the 50th to Thr of the 56th and ③ from Gln of the 89th to Thr of the 97th of the amino acid sequence represented by SEQ ID NO:17 of SEQUENCE LISTING.

(6) The H chain variable region of the monoclonal antibody produced by Hybridoma NOK1 consists of the amino acid sequence represented by SEQ ID NO:1, and the base sequence thereof is a base sequence represented by SEQ ID NO:2, while the L chain variable region thereof consists of the amino acid sequence represented by SEQ ID NO:3, and the base sequence thereof is a base sequence represented by SEQ ID NO:4.

(7) The H chain variable region of the monoclonal antibody produced by Hybridoma NOK2 consists of the amino acid sequence represented by SEQ ID NO:5, and the base sequence thereof is a base sequence represented by SEQ ID NO:6, while the L chain variable region thereof consists of the amino acid sequence represented by SEQ ID NO:7, and the base sequence thereof is a base sequence represented by SEQ ID NO:8.

(8) The H chain variable region of the monoclonal antibody produced by Hybridoma NOK3 consists of the amino acid sequence represented by SEQ ID NO:9, and the base sequence thereof is a base sequence represented by SEQ ID NO:10.

(9) The H chain variable region of the monoclonal antibody produced by Hybridoma NOK4 consists of the amino acid sequence represented by SEQ ID NO:11, and the base sequence thereof is a base sequence represented by SEQ ID NO:12, while the L chain variable region thereof consists of the amino acid sequence represented by SEQ ID NO:13, and the base sequence thereof is a base sequence represented by SEQ ID NO:14.

(10) The H chain variable region of the monoclonal antibody produced by Hybridoma NOK5 consists of the amino acid sequence represented by SEQ ID NO:15, and the base sequence thereof is a base sequence represented by SEQ ID NO:16, while the L chain variable region thereof consists of the amino acid sequence represented by SEQ ID NO:17, and the base sequence thereof is a base sequence represented by SEQ ID NO:18.

Examples of the preparation form of the therapeutic agent for hepatitis according to the present invention include injections, tablets, capsules, suppositories, nebulae, cream compositions, poultices and ophthalmic solutions like the conventional drugs and medicinal compositions each comprising an active ingredient. In the case of, for example, an injection, a solution containing the antibody is prepared under sterile conditions. A stabilizer such as mannitol, an excipient and the like may be added as auxiliary ingredients as needed. This solution may be charged into ampules, vials and the like and used as it is. Alternatively, the solution may be lyophilized as needed. In the case where the therapeutic agent for hepatitis according to the present invention is a dry product, it may be dissolved in distilled water for injection or the like before its administration. With respect to an administration method, it is only necessary to select a suitable method from oral administration, intravenous injection, inhalation, percutaneous administration, instillation, topical administration, subcutaneous administration and the like for administration. The therapeutic agent for hepatitis according to the present invention comprises, as an active ingredient, the antibody against Fas ligand, or the active fragment thereof in a proportion of generally 0.1–100 wt. %, preferably 0.5–70 wt. %. A dose of the therapeutic agent for hepatitis according to the present invention is within a range of generally 0.001–1,000 mg, preferably 0.01–600 mg in terms of the active ingredient per day for an adult. It goes without saying that the above dose is only a standard by and large, and a dose may be suitably selected according to the age, sex and weight of a patient to be administered, and moreover the kind and condition of a disease to be treated.

EXAMPLES

The present invention will hereinafter be described more specifically by the following Examples.

Example 1

(1) Preparation of Mouse Hepatocytes

Mouse hepatocytes were separated in accordance with the collagenase perfusion method described in Mitsui, et al., "Separation and Culture of Functional Cells", pp. 178–179 (issued by Maruzen Co., Ltd. in Jan. 30, 1987). More specifically, ① An anesthetized mouse was placed on an operating table and its abdomen was incised with surgical scissors in order of skin and abdominal muscle. Its bowels were pushed aside on the right side of the operator with alcoholized absorbent cotton squeezed well to fully expose its portal vein.

② A looped suture was put on the portal vein to rift the portal vein with the tip of ophthalmologic scissors. While washing out the blood flowed out of the cut part with a buffer solution for preperfusion dropped out of the distal end of a cannula, the cannula was rapidly inserted through the cut part of the portal vein, and the cut part was ligatured with the suture. At the same time, a subhepatic inferior vena cava was cut to discharge the washings. In this state, a peristaltic pump was actuated at a flow rate of 30 ml/min to continuously perfuse the buffer solution for preperfusion kept at 37° C.

③ The thorax was opened to expose a heart. After putting a looped suture on a thoracic inferior vena cava, the right atrium was incised with the ophthalmologic scissors, and another cannula was inserted into the thoracic inferior vena cava through the right atrium to ligature the cut part with the suture. In such a manner, the perfusate was recycled so as to circulate through the liver, flow into the thoracic inferior vena cava and return via the lately inserted cannula to a bottle in a thermostatic chamber. In this state, the perfusion was continued for 4–5 minutes, and the pump was stopped after confirmed that the perfusate was smoothly perfused. The circulating liquid was then replaced by a collagenase solution (about 100 ml) to resume the perfusion. When the perfusion with the collagenase solution was continued for 8–10 minutes, the liver was gradually digested to show such an appearance that the hepatic lobule came up, and an enzyme fluid came to exude from the surface.

In this state, the perfusion was stopped, and hepatic lobi were cut off with scissors while receiving them by a spatula, and transferred to a Petri dish. About 10 ml of MEM (product of Nissui K.K) were added to the Petri dish, and the hepatic lobi were lightly minced with a scalpel. As a result, digested hepatocytes were dispersed as if they were lysed. Then, 30 ml of MEM were added, light pipetting was conducted 2–3 times with a claviform Komagome pipette to further disperse the cells, and the dispersion was then filtered through a cell filter with 2–3 sheets of gauze overlapped each other.

A suspension containing roughly dispersed hepatocytes was first prepared in this manner. The following operation was then conducted to take only hepatic parenchymal cells out of this suspension.

The cell suspension was collected in a 50-ml cell-centrifuging tube and centrifuged at a low rate (50×g, 1 min) by a desk cooling centrifugal machine. Under these centrifuging conditions, the hepatic parenchymal cells were packed on the bottom of the centrifuging tube because such cells were larger than other cells. Nonparenchymal cells, traumatic cells, erythrocytes, cell fragments and the like did not precipitate, but remained in a supernatant. The supernatant was gently removed by a Komagome pipette, and a buffer solution for cell washing was newly added to lightly suspend the precipitated cells with the claviform Komagome pipette and at the same time, centrifuge them at a low rate. This operation was repeated 3 to 4 times, whereby almost homogeneous hepatic parenchymal cells were able to be obtained. After the centrifugation at a low rate, the viability of the resultant hepatic parenchymal cells is generally at least 90% (stain test with trypan blue), and their yield is 4 to $6 \times 10^7$ cells/g of liver.

Cytotoxicity of a soluble Fas ligand (i.e., sFasL) contained in a culture supernatant of a transfectant L5178Y-FasL, into which a Fas ligand has been transfected, against the thus-obtained mouse hepatocytes was investigated.

(2) Preparation of L5178Y-FasL

A method of transfecting a human Fas ligand into L5178Y is as follows.

Namely, each 1 unit of restriction enzymes, Xho I and Not I (both, products of Boehringer Co.) was added to 1 μg of a human Fas ligand gene integrated into PMKit Neo, an accessory buffer was added, and the reactants were allowed to react with each other at 37° C. for 2 hours. The reaction mixture was electrophoresed on 1% agarose gel. A band of about 850 pb corresponding to the Fas ligand was got out of the gel under UV irradiation.

DNA was extracted from this agarose gel using a GENECLEAN™ II kit (BIO101, product of Funakoshi K.K.). More specifically, an accessory NaI solution was added to the gel to incubate the gel at 65° C. for 10 minutes, thereby dissolving the gel in the solution. Glass milk was then added to the solution, and the mixture was rotationally stirred for 5 minutes to adsorb DNA on the glass milk. After this glass milk was washed three times with New-WASH solution, it was suspended in 10 μl of a TE buffer solution. The suspension was incubated at 65° C. for 3 minutes, thereby dissolving DNA out of the glass milk. A BCMGS$_{neo}$ vector (1 μg) was then treated with the restriction enzymes Xho I and Not I in the same manner as described above, and the treated vector was electrophoresed on 0.75% agarose gel, followed by purification with the GENECLEAN™ II kit.

The Fas ligand cDNA and BCMGS$_{neo}$ vector were then ligated by mixing them so as to give a molar ratio of the vector to cDNA of 1:2 and subjecting the mixture to a ligation reaction at 16° C. for 16 hours using a DNA ligation kit produced by Takara Shuzo Co., Ltd.

The reaction mixture thus obtained was mixed with *Escherichia coli* competent cells (product of Toyobo Co., Ltd.) to incubate the resultant mixture for 30 minutes on an ice bath and for 40 seconds at 42° C., thereby inserting DNA into *Escherichia coli*. After an SOC medium was added thereto, and shaking culture was conducted at 37° C. for 1 hour, the culture solution was poured into an LB agar medium containing ampicllin to conduct culture at 37° C. for 1 day. Thereafter, appeared colonies were cultured at 37° C. for 1 day in the LB medium, and the resultant plasmid (human Fas ligand-BCMGS$_{neo}$) was then recovered by the alkali method.

The transfection of this human Fas ligand-BCMGS$_{neo}$ into L5178Y cells was carried out in a proportion of (1 μg of the human Fas ligand-BCMGS$_{neo}$)/(1×10$^6$ L5178Y cells) in accordance with the electroporation method under conditions that a Gene Pulser (gene transfer apparatus, manufactured by Bio-Rad Co.) was used at 296 V and 960 μF. The cells were suspended again in 5 ml of a 10% FCS-RPMI 1640 medium. The cell suspension was poured into a 6-well plate to conduct culture. At this time, G418 (product of GIBCO Co.) was added to the medium so as to give a concentration of 0.4 mg/ml. After culturing for 10 days, colonies were obtained, so that cells were cloned by the limiting dilution technique. A clone having the highest human Fas ligand mRNA content was sorted from the thus-obtained clones by the northern hybridization technique and cultured. The cells thus obtained were regarded as the Fas ligand-L5178Y cells (i.e., L5178Y-FasL).

(3) Investigation as to Cytotoxicity of FasL Against Mouse Hepatocytes:

① Preparation of Soluble FasL (sFasL)

L5178Y-FasL was cultured for 4 days at a concentration of $5 \times 10^5$ cells/ml using 30 ml of a 10% FCS.RPMI 1640 medium in a 75-cm$^2$ culture flask, and a culture supernatant thereof was collected. The collected supernatant (sFasL) was sterilized through a filter having a pore size of 0.45 μm and conserved.

② Preparation of Target Cells

Target cells were obtained by adjusting the hepatic parenchymal cells prepared in the item (1) to $2 \times 10^5$ cells/ml with a 10% FCS.L-15 medium.

③ Assay

The sFasL molecule prepared in the step ① was diluted to 1/12 with a 10% FCS.RPMI 1640 medium. A 96-well flat-bottomed plate (manufacture by Corning Co.) was used, and 25 μl of the diluted solution were added to each well. Then, 25 μl of a 10% FCS.L-15 medium were added. For the sake of comparison, those obtained by respectively adding 25 μl of an anti-mouse Fas antibody (Jo-2; product of Phar-Mingen Co.) and 25 μl of TNF (product of Sigma Co.) at a concentration of 10 μl/ml were used. To each well of these plates were added 50 μl of the target cells prepared in the step ②. Thereafter, the cells were incubated for 12 hours under conditions of 370° C. and 5% $CO_2$.

ALAMAR BLUE (cell fluorescence labeling kit, product of Cosmo-Bio Co.) was added in a proportion of 10 μl/well, followed by a further incubation for 4 hours under conditions of 37° C. and 5% $CO_2$.

Thereafter, a FLUOROSGAN™ II (spectrofluorometer, manufactured by Titertec Co.) was used to measure fluorescence.

The results are shown collectively in Table 1. As apparent from Table 1, the viability of the hepatic parenchymal cells was reduced only by sFasL.

TABLE 1

| Additive | Viability (%) |
| --- | --- |
| Not added | 100 |
| sFasL | 0.5 |
| Anti-Fas antibody | 99 |
| TNF | 98 |

(4) Effect of Anti-Human FasL Antibody on Cytotoxicity of FasL Against Mouse Hepatocytes As described above, FasL was found to exhibit the cytotoxicity against the hepatic parenchymal cells. Therefore, whether this cytotoxic reaction can be inhibited by the anti-human FasL antibody or not was then investigated. Namely, the investigation was made in the same system as in the item (3).

The sFasL prepared in the step ① of the item (3) was diluted to 1/12 with a 10% FCS.RPMI 1640 medium. A 96-well flat-bottomed plate was used, and 25 μl of the diluted solution were added to each well. The anti-human FasL antibody (NOK1) diluted to 10 μg/ml with a 10% FCS.L-15 medium was then added in a proportion of 25 μl/well, and the plate was incubated for 1 hour under conditions of 37° C. and 5% $CO_2$. Thereafter, the hepatic parenchymal cells ($2 \times 10^5$ cells/ml) were added in a proportion of 50 μl/well and incubated for 12 hours under conditions of 37° C. and 5% $CO_2$.

ALAMAR BLUE (product by Cosmo-Bio Co.) was added in a proportion of 10 μl/well, followed by a further incubation for 4 hours under conditions of 37° C. and 5% $CO_2$. Thereafter, a FLUOROSCAN™ II was used to measure the fluorescence intensity of the dye decomposed by the viable cells.

The results are shown in Table 2. As apparent from Table 2, the apoptosis of the hepatocytes was inhibited by the addition of the anti-FasL antibody.

TABLE 2

| Additive | Viability (%) |
| --- | --- |
| Not added | 100 |
| sFasL | 0.5 |
| sFasL + anti-FasL antibody | 99 |

Namely, it was confirmed that in the in vitro experimental system, the apoptosis of the hepatocytes via the FasL can be inhibited by the anti-FasL antibody.

(5) Investigation as to Prevention of Hepatitis by Administration of Anti-FasL Antibody in Experimental Hepatitis Model System in SCID Mouse A suspension of human peripheral blood mononuclear cells (PBMC, $5 \times 10^7$ cells) in 1 ml of PBS was intraperitoneally administered to an SCID™ mouse (female aged 8 weeks, product of Charles River Co.). After 6 to 12 hours, a suspension of 20 mg of D-galactosamine (product of Wako K.K.) and 10 μg of SEB (staphylococcal enterotoxin B; product of Sigma Co.) in 1 ml of PBS was further intraperitoneally administered. Incidentally, when the anti-FasL antibody was administered, 500 μg of the antibody were intraperitoneally administered 30 minutes before D-galactosamine and SEB were administered.

Thereafter, the levels of GOT (glutamic-oxaloacetic transaminase) and GPT (glutamic-pyruvic transaminase) in blood after 12 hours were determined, and staining of the hepatocytes was conducted after 24 hours.

As a result, survival after 24 hours was significantly recognized in the group administered with the anti-FasL antibody compared with the control group administered with no antibody. Besides, it was recognized that the levels of GOT and GPT after 12 hours in the administered group differ by 2 figures from those in the control, and are recovered near to normal values. The results are shown in Table 3.

TABLE 3

| Anti-FasL antibody | Number of survivors | GOT | GPT |
| --- | --- | --- | --- |
| + | 4/4 | 350 | 210 |
| − | 0/4 | >10000 | >10000 |

As a result, it was demonstrated that the antibody against human Fas ligand according to the present invention is useful as a therapeutic agent for hepatitis.

Example 2

Sequencing of V Region Genes of Anti-FasL Antibodies

Using the hybridomas NOK1 to NOK5, variable region (V region) genes of monoclonal antibodies against Fas ligand were sequenced.

1. Preparation of cDNA (1) The hybridomas NOK1 to NOK5 were separately cultured in 25-cm$^3$ flasks. After cultured cells were collected and centrifugally washed with PBS, the cells were suspended in 1 ml of PBS to count the number of cells. The cells ($1 \times 10^6$ cells) were placed in a sterile Eppendorf tube. A supernatant was drawn out by centrifugation to tap the resultant pellets.

(2) RNA$_{zo1}$B™ (product of Cosmo-Bio, 200 µl) was added to the tube, and the mixture was fully stirred with a tip of a pipetteman, thereby dissolving the cells therein. After 20 µl of chloroform were added, and the tube was shaken, it was left to stand for 5 minutes on an ice bath. After the mixture was centrifuged for 15 minutes at 4° C. and 15,000 rpm, a colorless and transparent portion of an upper layer was recovered and transferred to a new tube. After the upper portion was centrifuged for 15 minutes at 4° C. and 15,000 rpm, a supernatant was thrown out, 800 µl of 75% ethanol were added to the residual pellets, and the mixture was left to stand for 30 minutes at −20° C. After the mixture was centrifuged for 15 minutes at 4° C. and 15,000 rpm, 11.5 µl of distilled water were added to the pellets.

(3) Oligo dT (0.5 mg/ml; 0.5 µl) was added, and the mixture was left to stand for 10 minutes at 70° C. and for 5 minutes on an ice bath.

TABLE 4

| 5 × RT buffer | 4 µl |
|---|---|
| 10 mM dNTPmix | 1 µl |
| Superscript RTase (product of Stratagene) | 1 µl |

The individual components shown in Table 4 were added, and the mixture was left to stand for 5 minutes at 90° C. and then for 5 minutes on an ice bath.

(4) RNaseH (1 µl) was added, and the resultant mixture was left to stand for 20 minutes at 37° C. In such a manner, a mixture of cDNAs was obtained.

2. PCR (1) The cDNAs obtained by the above-described process were used to conduct PCR under conditions shown in the following Table 5.

TABLE 5

|  | VH | VL |
|---|---|---|
| cDNA | 2 µl | 2 µl |
| dNTPmix | 1 µl | 1 µl |
| Primer (product of Pharmacia) | 2 µl | 1 µl |
| 10 × PCR buffer | 4 µl | 4 µl |
| DDW | 30.5 µl | 31.5 µl |
| Ampli-Tag | 0.5 µl | 0.5 µl |

After the mixture was topped with 40 µl of mineral oil and left to stand for 5 minutes at 94° C., an amplification reaction was carried out by repeating the cycle of "2 minutes at 55° C., 3 minutes at 72° C. and 1 minute at 94° C." 30 cycles. The reaction mixture was then left to stand for 2 minutes at 55° C. and for 10 minutes at 72° C.

(2) The reaction mixture (4 µl) was checked by mini gel electrophoresis (1.5% agarose gel). The result is illustrated in FIG. 1. It was confirmed that DNA fragments except for the L chain of the monoclonal antibody NOK3 were amplified by PCR.

3. Recovery of V$_H$ and V$_L$ Fragments (1) The PCR products prepared above were subjected to mini gel electrophoresis (1.5% agarose gel) to get bands of VH (H chain variable region) and VL (L chain variable region) out of the gel.

Figure 2:
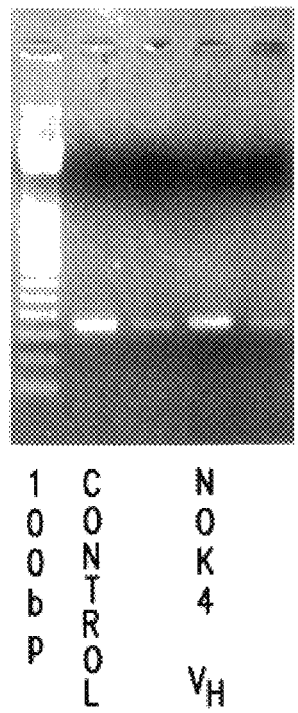
FIG. 2 is a mini gel electrophorogram of a product in PCR of a VL gene of NOK4.

(2) The PCR products were recovered by GENECLEAN™, and the bands were checked by mini gel electrophoresis (1.5% agarose gel). As an example, the result as to the VH of NOK4 is illustrated in FIG. 2.

4. Ligation

A TA CLONING KIT™ (product of Invitrogen Co.) shown in the following Table 6 was used to conduct ligation of DNA.

TABLE 6

| ADDW | 5 µl |
|---|---|
| 10 × Ligation buffer | 1 µl |
| PCR vector | 2 µl |
| PCR product | 1 µl |
| T4DNA Ligase | 1 µl |

The reaction was conducted overnight at 14° C. to obtain a ligation mixture.

5. Transformation

TA CLONING KIT™ was used to conduct transformation.

(1) After 2 µl of 0.5 M β-mercaptoethanol and the ligation mixture prepared above were added to 50 µl of the cells on an ice bath, and the resultant mixture was left to stand for 30 minutes, it was left to stand for 30 seconds on a hot water bath of 42° C. and then for 20 minutes on an ice bath. An SOC medium (450 µl) was added to the mixture, and incubation was conducted at 37° C. for 1 hour (225 rpm).

(2) The cells were then spread on LB agar plates (+Amp, X-Gal, IPTG). The respective samples were of 50 µl, 100 µl and 200 µl. The samples were incubated at 37° C. for 18 hours and then left to stand for 2 hours at 4° C. As a result, white and blue colonies were expressed.

6. Mini Culture (1) Four white colonies were taken out of each sample plate.

(2) One colony of them was added to 3 ml of an LB medium (+Amp), and the medium was shaken overnight at 37° C.

7. Mini Preparation (1) A culture solution (1.5 ml) was taken in an Eppendorf tube. (It was spread on an LB plate for conservation and cultured at 37° C.) The culture solution was centrifuged for 2 minutes at 4° C. and 6,000 rpm.

(2) After 100 µl of Solution 1 (5 mg/ml of lysozyme) were added to the precipitated pellets, and the mixture was left to stand for 5 minutes at room temperature, 200 µl of Solution 2 (mixed gently for 5 minutes on an ice bath) and then 150 µl of Solution 3 (mixed for 15 minutes on an ice bath) were added to the mixture. The resultant mixture was then centrifuged for 5 minutes at 4° C. and 12,000 rpm. Incidentally, Solutions 1 and 2 correspond to solution I and II described in "Molecular Cloning" (Cold Spring Harbor Laboratory Press), respectively.

(3) A supernatant was taken in a new Eppendorf tube. An equal volume of phenol was added thereto, and the resultant mixture was then centrifuged for 1 minute at 12,000 rpm.

(4) A supernatant was taken in a new Eppendorf tube. An equal volume of a mixture of CHCl$_3$:iAA (99:1) was added thereto, and the resultant mixture was then centrifuged for 1 minute at 12,000 rpm.

(5) A supernatant was taken in a new Eppendorf tube. To the supernatant were added 1 µl of Mussel glycogen and 900 µl of ethanol, and the resultant mixture was left to stand for 30 minutes at −80° C. and then centrifuged for 5 minutes at 4° C. and 15,000 rpm.

(6) Precipitate was dried. To the dried product were added 20 µl of TE and 1 µl of RNase A (5 mg/ml), and the resultant mixture was left to stand for 20 minutes at 65° C.

(7) In the above-described manner, plasmid DNAs were obtained.

Figure 3:
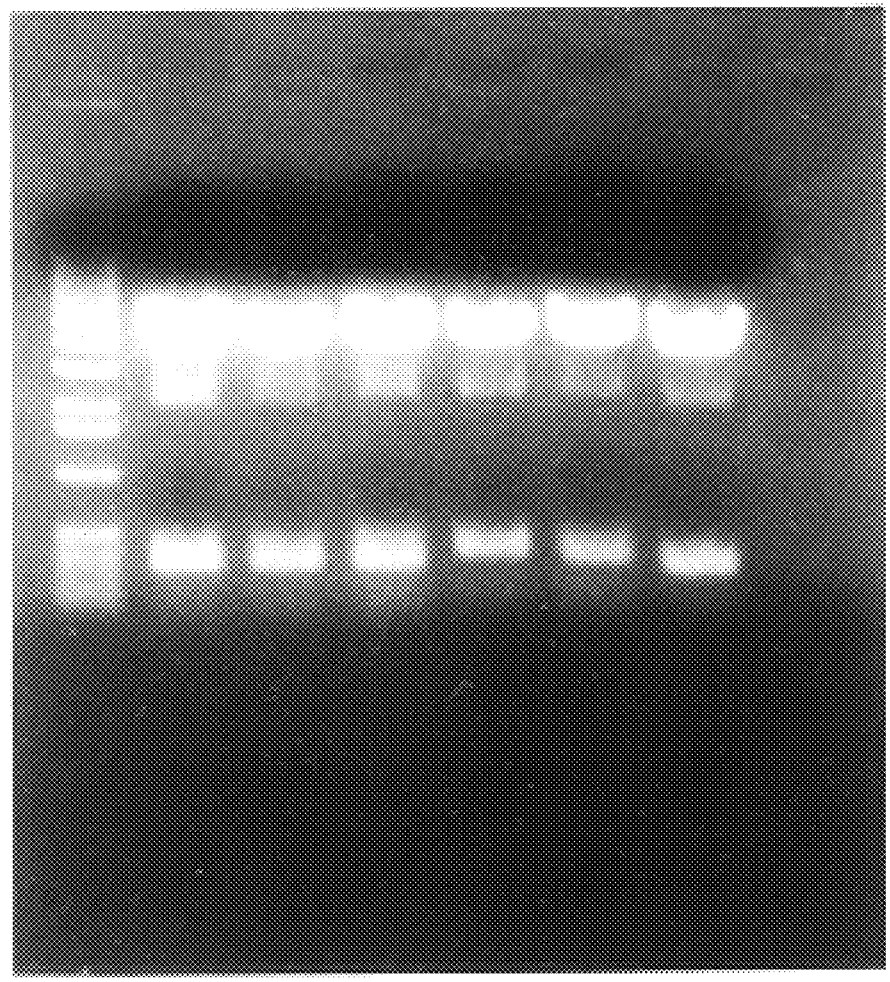
FIG. 3 is a mini gel electrophorogram of plasmid DNAS.

(8) Mini gel electrophoresis was performed under conditions shown in the following Table 7 to check bands. The results as to NOK4 $V_L$, NOK5 $V_H$ and NOK5 $V_L$ are illustrated in FIG. 3.

TABLE 7

| H Buf. | 1 μl |
|---|---|
| EcoR I | 1 μl (1U) |
| DNA | 1 μl |
| ADDW | 7 μl |

The sample was incubated at 37° C. for 1 hour and then added to 0.75% agarose gel to conduct electrophoresis.

8. DNA Sequensing (1) Each plasmid DNA was taken out in an amount of 1 μl and diluted with 99 μl of TE.

(2) The A260 value thereof was determined to calculate its DNA value (A260 of 1.0=50 μg/ml).

(3) Based on the A260 value, the plasmid DNA was diluted with TE in such a manner that the concentration of DNA amounts to 1 μg/μl.

(4) DNA sequensing (ABI Model 373A) was performed by the Dye terminator method.

9. Analysis of V Regions

Based on the DNA sequences thus obtained, the amino acid sequences of the V regions were determined by computer analysis. The results are illustrated in FIG. 4 (amino acid sequences of the VH regions of the monoclonal antibodies NOK1 to NOK5) and FIG. 5 (amino acid sequences of the VL regions of the monoclonal antibodies NOK1, NOK2, NOK4 and NOK5). In these drawings, portions enclosed with a rectangle represent hypervariable regions (CDR1 to CDR3).

INDUSTRIAL APPLICABILITY

The therapeutic agents for hepatitis according to the present invention are medicines useful for the treatment of hepatitis. The therapeutic agents for hepatitis according to the present invention are particularly effective for the treatment of hepatitis caused by the death of hepatic parenchymal cells due to apoptosis. The reason for it is that the therapeutic agents for hepatitis according to the present invention can inhibit apoptosis of the hepatic parenchymal cells via FasL and Fas.

INTERNATIONAL DEPOSITARY INSTITUTION

Hybridomas NOK1 to NOK5 are deposited in the following international depositary institution with the following respective accession numbers and deposition dates.

Name: National Institute of Bioscience and Human-Technology,

Agency of Industrial Science and Technology, Ministry of International Trade and Industry.

Address: 1-3, Higashi 1-chome, Tsukuba-shi, Ibaraki-ken 305, Japan.

Accession numbers and deposition dates:

① Hybridoma NOKl FERM BP-5044; Mar. 20, 1995
② Hybridoma NOK2 FERM BP-5045; Mar. 20, 1995
③ Hybridoma NOK3 FERM BP-5046; Mar. 20, 1995
④ Hybridoma NOK4 FERM BP-5047; Mar. 20, 1995
⑤ Hybridoma NOK5 FERM BP-5048; Mar. 20, 1995

We claim:

1. A therapeutic agent for hepatitis, comprising an antibody against a human Fas ligand, or an active fragment of the antibody as an active ingredient, wherein the antibody is a monoclonal antibody produced by any one of respective hybridoma cell lines deposited as Accession Nos. FERM BP-5044, FERM BP-5045, FERM BP-5046, FERM BP-5047 and FERM BP-5048 in National Institute of Bioscience and Human-Technology, Agency of Industrial Science and Technology.

2. A therapeutic agent for hepatitis, comprising an antibody against a human Fas ligand, or an active fragment of the antibody as an active ingredient, wherein the antibody or the active fragment is a chimera antibody molecule at least containing an H chain variable region and/or an L chain variable region of a monoclonal antibody which specifically reacts to the human Fas ligand, and further wherein the chimara antibody molecule at least contains an amino acid sequence of a hypervariable region of a monoclonal antibody produced by any one of respective hybridoma cell lines deposited as Accession Nos. FERM BP-5044, FERM BP-5045, FERM BP-5046, FERM BP-5047 and FERM BP-5048 in National Institute of Bioscience and Human-Technology, Agency of Industrial Science and Technology.

3. A therapeutic agent for hepatitis, comprising an antibody against a human Fas ligand, or an active fragment of the antibody as an active ingredient, wherein the antibody or the active fragment is a chimera antibody molecule at least containing an H chain variable region and/or an L chain variable region of a monoclonal antibody which specifically reacts to the human Fas ligand, and further wherein the chimara antibody molecule at least contains an amino acid sequence of a variable region of a monoclonal antibody produced by any one of respective hybridoma cell lines deposited as Accession Nos. FERM BP-5044, FERM BP-5045, FERM BP-5046, FERM BP-5047 and FERM BP-5048 in National Institute of Bioscience and Human-Technology, Agency of Industrial Science and Technology.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 120 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Val Gln Leu Gln Glu Ser Gly Pro Glu Leu Val Lys Pro Gly Ala Ser
1               5                   10                  15

Val Lys Ile Ser Cys Lys Ala Ser Gly Tyr Ala Phe Ser Ser Ser Trp
            20                  25                  30

Met Asn Trp Val Lys Gln Arg Pro Gly Lys Gly Leu Glu Trp Ile Gly
        35                  40                  45

Arg Ile Tyr Pro Gly Asp Gly Asp Thr Asn Asp Asn Gly Lys Phe Lys
    50                  55                  60

Gly Lys Ala Thr Leu Thr Ala Asp Lys Ser Ser Ser Thr Ala Tyr Met
65                  70                  75                  80

Gln Leu Ser Ser Leu Thr Ser Glu Asp Ser Ala Val Tyr Phe Cys Ala
                85                  90                  95
```

```
Arg Ser Tyr Tyr Tyr Asp Gly Ser Pro Trp Phe Thr Tyr Trp Gly Gln
            100                 105                 110

Gly Thr Thr Val Thr Val Ser Ser
        115                 120

(2) INFORMATION FOR SEQ ID NO:2:

(i) SEQUENCE CHARACTERISTICS:
        (A) LENGTH: 360 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:2:

GTGCAGCTGC AGGAGTCTGG ACCTGAGCTG GTGAAGCCTG GGGCCTCAGT GAAGATTTCC        60

TGCAAGGCTT CTGGCTATGC ATTCAGTAGC TCCTGGATGA ACTGGGTGAA GCAGAGGCCT       120

GGAAAGGGTC TTGAGTGGAT TGGACGAATT TATCCTGGAG ATGGAGATAC TAACGACAAC       180

GGGAAGTTCA AGGGCAAGGC CACACTGACC GCAGACAAAT CCTCCAGCAC AGCCTACATG       240

CAACTCAGCA GTCTGACATC TGAGGACTCT GCGGTCTACT TCTGTGCAAG ATCGTATTAC       300

TACGATGGTA GCCCCTGGTT TACTTACTGG GGCCAAGGGA CCACGGTCAC CGTCTCCTCA       360

(2) INFORMATION FOR SEQ ID NO:3:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Asp Ile Gln Met Thr Gln Ser Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Phe Cys Gln Gln Tyr Ser Glu Phe Pro Trp
                85                  90                  95

Thr Phe Gly Gly Gly Thr Lys Leu Glu Ile Lys Arg
            100                 105

(2) INFORMATION FOR SEQ ID NO:4:

(i) SEQUENCE CHARACTERISTICS:
        (A) LENGTH: 324 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:4:
```

```
GACATCCAGA TGACGCAGTC TCCATCCTCC CTGTCTGCCT CTCTGGGAGA CAGAGTCACC    60

ATCAGTTGCA GGGCAAGTCA GGATATTAGC AATTATTTAA ACTGGTATCA GCAGAAACCA   120

GATGGAACTG TTAAACTCCT GATCTACTAC ACATCAAGAT TACACTCAGG AGTCCCATCA   180

AGGTTCAGTG GCAGTGGGTC TGGGACAGAT TATTCTCTCA CCATCAGCAA CCTGGAACCT   240

GAAGATATTG CCACTTACTT TTGTCAGCAA TATAGTGAAT TTCCGTGGAC GTTCGGTGGA   300

GGCACCAAGC TGGAAATCAA ACGG                                         324
```

(2) INFORMATION FOR SEQ ID NO:5:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Val Gln Leu Gln Gln Ser Gly Ala Glu Leu Val Arg Pro Gly Thr Ser
1               5                  10                  15

Val Lys Met Ser Cys Lys Ala Ala Gly Tyr Thr Phe Thr Asn Tyr Trp
                20                  25                  30

Ile Gly Trp Val Lys Gln Arg Pro Gly His Gly Leu Glu Trp Ile Gly
            35                  40                  45

Tyr Leu Tyr Pro Gly Gly Leu Tyr Thr Asn Tyr Asn Glu Lys Phe Lys
        50                  55                  60

Gly Lys Ala Thr Leu Thr Ala Asp Thr Ser Ser Ser Thr Ala Tyr Met
65                  70                  75                  80

Gln Leu Ser Ser Leu Thr Ser Glu Asp Ser Ala Ile Tyr Tyr Cys Ala
                85                  90                  95

Arg Tyr Arg Asp Tyr Asp Tyr Ala Met Asp Tyr Trp Gly Gln Gly Thr
                100                 105                 110

Thr Val Thr Val Ser Ser
            115
```

(2) INFORMATION FOR SEQ ID NO:6:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:6:

```
GTGCAGCTGC AGCAGTCAGG AGCTGAGCTG GTAAGGCCTG GGACTTCAGT GAAGATGTCC    60

TGCAAGGCTG CTGGATACAC CTTCACTAAC TACTGGATAG TTGGGTAAA GCAGAGGCCT    120

GGACATGGCC TTGAGTGGAT TGGATATCTT TACCCTGGAG GTCTTTATAC TAACTACAAT   180

GAGAAGTTCA AGGGCAAGGC CACACTGACT GCAGACACAT CCTCCAGCAC AGCCTACATG   240

CAGCTCAGCA GCCTGACATC TGAGGACTCT GCCATCTATT ACTGTGCAAG ATACAGGGAT   300

TACGACTATG CTATGGACTA CTGGGGCCAA GGGACCACGG TCACCGTCTC CTCA         354
```

(2) INFORMATION FOR SEQ ID NO:7:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Asp Val Leu Met Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Ser
            20                  25                  30

Asp Gly Phe Thr Tyr Leu Gly Trp Cys Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Asn Tyr Leu Pro Leu Thr Phe Gly Ser Gly Thr Lys Leu Glu Ile Lys
            100                 105                 110

Arg
```

(2) INFORMATION FOR SEQ ID NO:8:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:8:

```
GATGTTTTGA TGACCCAAAC TCCACTCTCT CTGCCTGTCA ATATTGGAGA TCAAGCCTCT      60

ATCTCTTGCA AGTCTACTAA GAGCCTTCTG AATAGTGATG GATTCACTTA TTTGGGCTGG     120

TGCCTGCAGA AGCCAGGCCA GTCTCCACAG CTCCTAATAT ATTTGGTTTC TAATCGATTT     180

TCTGGAGTTC CAGACAGGTT CAGTGGTAGT GGGTCAGGGA CAGATTTCAC CCTCAAGATC     240

AGCAGAGTGG AGGCTGAGGA TTTGGGAGTT TATTATTGCT TCCAGAGTAA CTATCTTCCT     300

CTTACGTTCG GATCGGGGAC CAAGCTGGAA ATAAAACGG                            339
```

(2) INFORMATION FOR SEQ ID NO:9:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Val Lys Leu Gln Glu Ser Gly Pro Glu Leu Val Lys Pro Gly Ala Ser
1               5                   10                  15

Val Lys Ile Ser Cys Lys Ala Ser Gly Tyr Ala Phe Ser Ser Ser Trp
            20                  25                  30
```

```
Met Asn Trp Val Lys Gln Arg Pro Gly Lys Gly Leu Glu Trp Ile Gly
         35                  40                  45

Arg Ile Tyr Pro Val Asn Gly Asp Thr Asn Tyr Asn Gly Lys Phe Lys
         50                  55                  60

Gly Lys Ala Thr Leu Thr Ala Asp Lys Ser Ser Ser Thr Ala Tyr Met
 65                  70                  75                  80

Gln Leu Ser Ser Leu Thr Ser Glu Asp Ser Ala Val Tyr Phe Cys Ala
                 85                  90                  95

Thr Asp Gly Tyr Trp Tyr Phe Asp Val Trp Gly Gln Gly Thr Thr Val
                100                 105                 110

Thr Val Ser Ser
        115
```

(2) INFORMATION FOR SEQ ID NO:10:

(i) SEQUENCE CHARACTERISTICS:
        (A) LENGTH: 348 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:10:

```
GTGAAGCTGC AGGAGTCTGG ACCTGAGCTG GTGAAGCCTG GGGCCTCAGT GAAGATTTCC    60

TGCAAGGCTT CTGGCTATGC ATTCAGTAGC TCCTGGATGA ACTGGGTGAA ACAGAGGCCT   120

GGGAAGGGTC TGAGTGGATT GGACGGATTT ATCCTGTAA ATGGAGATAC TAACTACAAT    180

GGGAAGTTCA AGGCAAGGC CACACTGACT GCAGACAAAT CCTCCAGCAC AGCCTACATG    240

CAACTCAGCA GCCTGACATC TGAGGACTCT GCGGTCTACT TCTGTGCAAC CGATGGTTAC   300

TGGTACTTCG ATGTCTGGGG CCAAGGGACC ACGGTCACCG TCTCCTCA                348
```

(2) INFORMATION FOR SEQ ID NO:11:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Val Gln Leu Gln Glu Ser Gly Pro Gly Leu Val Lys Pro Ser Gln Ser
 1               5                  10                  15

Leu Ser Leu Thr Cys Ser Val Thr Gly Tyr Ser Ile Thr Ser Gly Tyr
                 20                  25                  30

Tyr Trp Asn Trp Ile Arg Gln Phe Pro Gly Asn Lys Leu Glu Trp Met
         35                  40                  45

Gly Tyr Ile Ser Tyr Asp Gly Ser Asn Asn Tyr Asn Pro Ser Leu Lys
         50                  55                  60

Asn Arg Ile Ser Ile Thr Arg Asp Thr Ser Lys Asn Gln Phe Phe Leu
 65                  70                  75                  80

Lys Leu Asn Ser Val Thr Thr Glu Asp Thr Ala Thr Tyr Tyr Cys Ala
                 85                  90                  95

Val Tyr Tyr Tyr Asp Gly Ser Ser Phe Asp Tyr Trp Gly Gln Gly Thr
                100                 105                 110

Thr Val Thr Val Ser Ser
        115
```

(2) INFORMATION FOR SEQ ID NO:12:

(i) SEQUENCE CHARACTERISTICS:
        (A) LENGTH: 354 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:12:

```
GTGCAGCTGC AGGAGTCTGG ACCTGGCCTC GTGAAACCTT CTCAGTCTCT GTCTCTCACC      60

TGCTCTGTCA CTGGCTACTC CATCACCAGT GGTTATTACT GGAACTGGAT CCGGCAGTTT     120

CCAGGAAACA AACTGGAATG GATGGGCTAC ATAAGCTACG ATGGTAGCAA TAACTACAAC     180

CCATCTCTCA AAAATCGAAT CTCCATCACT CGTGACACAT CTAAGAACCA GTTTTTCCTG     240

AAGTTGAATT CTGTGACTAC TGAGGACACA GCCACATATT ACTGTGCCGT TTATTACTAC     300

GATGGTAGCT CTTTTGACTA CTGGGGCCAA GGGACCACGG TCACCGTCTC CTCA           354
```

(2) INFORMATION FOR SEQ ID NO:13:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Asp Ile Val Leu Thr Gln Ser Pro Ala Ser Leu Ala Val Ser Leu Arg
1               5                   10                  15

Gln Arg Ala Thr Ile Ser Cys Arg Ala Ser Glu Gly Val Asp Ser Tyr
            20                  25                  30

Gly Ile Ser Phe Met His Trp Tyr Gln Gln Lys Pro Gly Gln Pro Pro
        35                  40                  45

Lys Leu Leu Ile Tyr Arg Ala Ser Tyr Leu Lys Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Leu Glu Ile Lys Arg
            100                 105                 110
```

(2) INFORMATION FOR SEQ ID NO:14:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:14:

```
GACATTGTGC TGACCCAATC TCCAGCTTCT TTGGCTGTGT CTCTAAGGCA GAGGGCCACC      60

ATATCCTGCA GAGCCAGTGA AGGTGTTGAT AGTTATGGCA TTAGTTTTAT GCACTGGTAC     120

CAGCAGAAAC CAGGACAGCC ACCCAAACTC CTCATCTATC GTGCATCCTA CCTAAAATCT     180
```

```
GGGGTCCCTG CCAGGTTCAG TGGTAGTGGG TCTAGGACAG ACTTCACCCT CACCATTGAT      240

CCTGTGGAGG CTGATGATGC TGCAACCTAT TACTGTCAGC AAAATAATGA GGATCCGTGG      300

ACGTTCGGTG GAGGCACCAA GCTGGAAATC AAACGG                                336
```

(2) INFORMATION FOR SEQ ID NO:15:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Val Gln Leu Gln Glu Ser Gly Ala Glu Pro Ala Lys Pro Gly Ala Ser
1               5                   10                  15

Val Lys Met Ser Cys Lys Ala Ser Gly Tyr Thr Phe Thr Thr Tyr Trp
            20                  25                  30

Met His Trp Val Lys Gln Arg Pro Gly Gln Gly Leu Glu Trp Ile Gly
        35                  40                  45

Tyr Ile Asn Pro Ser Ser Gly Tyr Thr Glu Tyr Asn Gln Lys Phe Lys
    50                  55                  60

Asp Lys Ala Thr Leu Thr Ala Asp Lys Ser Ser Ser Thr Ala Tyr Met
65                  70                  75                  80

Gln Leu Ile Ser Leu Thr Ser Glu Asp Ser Ala Val Tyr Tyr Cys Ala
                85                  90                  95

Arg Arg Gly Asn Tyr Tyr Tyr Phe Asp Tyr Trp Gly Gln Gly Thr Thr
            100                 105                 110

Val Thr Val Ser Ser
        115
```

(2) INFORMATION FOR SEQ ID NO:16:

(i) SEQUENCE CHARACTERISTICS:
        (A) LENGTH: 351 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:16:

```
GTGCAGCTGC AGGAGTCTGG GGCTGAACCG GCAAAACCTG GGGCCTCAGT GAAGATGTCC       60

TGCAAGGCTT CTGGCTACAC CTTTACTACC TACTGGATGC ACTGGGTAAA ACAGAGGCCT      120

GGACAGGGTC TGGAATGGAT TGGATACATT AATCCTAGCA GTGGTTATAC TGAGTACAAT      180

CAGAAGTTCA AGGACAAGGC CACATTGACT GCAGACAAAT CCTCCAGCAC AGCCTACATG      240

CAACTAATCA GCCTGACATC TGAGGACTCT GCAGTCTATT ACTGTGCAAG AAGGGGTAAT      300

TACTACTACT TTGACTACTG GGGCCAAGGG ACCACGGTCA CCGTCTCCTC A               351
```

(2) INFORMATION FOR SEQ ID NO:17:

(i) SEQUENCE CHARACTERISTICS:
        (A) LENGTH: 105 amino acids
        (B) TYPE: amino acid
        (C) STRANDEDNESS: single
        (D) TOPOLOGY: linear -continued

```
    (ii) MOLECULE TYPE: peptide (xi) SEQUENCE DESCRIPTION: SEQ ID NO:17:

Asp Val Leu Met Thr Gln Thr Pro Lys Phe Leu Pro Val Ser Ala Gly
1               5                   10                  15

Asp Arg Val Thr Met Thr Cys Lys Ala Ser Gln Ser Val Gly Asn Asn
                20                  25                  30

Val Ala Trp Tyr Gln Gln Lys Pro Gly Gln Ser Pro Lys Leu Leu Ile
            35                  40                  45

Tyr Tyr Thr Ser Asn Arg Tyr Thr Gly Val Pro Asp Arg Phe Thr Gly
    50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Tyr
                85                  90                  95

Thr Phe Gly Ser Gly Thr Lys Leu Glu
                100             105

(2) INFORMATION FOR SEQ ID NO:18:

(i) SEQUENCE CHARACTERISTICS:
        (A) LENGTH: 315 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:18:

GATGTTTTGA TGACCCAAAC TCCAAAATTC CTGCCTGTAT CAGCAGGAGA CAGGGTTACC         60

ATGACCTGCA AGGCCAGTCA GAGTGTGGGT AATAATGTGG CCTGGTACCA ACAGAAGCCA        120

GGACAGTCTC CTAAACTGCT GATATACTAT ACATCCAATC GCTACACTGG AGTCCCTGAT        180

CGCTTCACTG GCAGTGGATC TGGGACAGAT TTCACTTTCA CCATCAGCAG TGTGCAGGTT        240

GAAGACCTGG CAGTTTATTT CTGTCAGCAG CATTATAGCT CTCCGTATAC GTTCGGATCG        300

GGGACCAAGC TGGAG                                                        315
```